United States Patent [19]

Son et al.

[11] Patent Number: 4,650,903
[45] Date of Patent: Mar. 17, 1987

[54] OLIGOMERIC AMIDES AS SYNERGISTS FOR ANTIOXIDANTS AND UV STABILIZERS

[75] Inventors: Pyong-Nae Son, Akron; John T. Lai, Broadview Heights, both of Ohio

[73] Assignee: The BFGoodrich Company, Akron, Ohio

[21] Appl. No.: 622,905

[22] Filed: Jun. 21, 1984

[51] Int. Cl.$^4$ .................. C07C 103/00; C07C 103/20; C08K 5/32; C08K 5/34
[52] U.S. Cl. .................................... 564/153; 564/155; 544/358; 544/359; 544/406; 523/1; 523/461; 523/508; 524/86; 524/100; 524/210; 524/212
[58] Field of Search ............... 564/153, 155; 544/358, 544/359, 406; 524/86, 100, 210, 212; 523/461, 1, 508

[56] References Cited

U.S. PATENT DOCUMENTS

| | | | |
|---|---|---|---|
| 4,058,523 | 11/1977 | Mori et al. | 564/153 X |
| 4,139,605 | 2/1979 | Felder et al. | 564/153 X |
| 4,239,747 | 12/1980 | Pfeiffer et al. | 564/153 X |
| 4,250,294 | 2/1981 | Hagel et al. | 564/155 X |
| 4,336,116 | 6/1982 | Schupp et al. | 564/153 X |

Primary Examiner—Paul F. Shaver
Attorney, Agent, or Firm—G. A. Kap; A. A. Csontos

[57] ABSTRACT

Oligomeric amides having the general structure

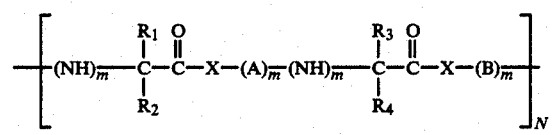

are useful as stabilizers for polymers and are prepared in a one-step synthesis by reacting a suitable amine with an appropriate ketone and chloroform.

14 Claims, No Drawings

OLIGOMERIC AMIDES AS SYNERGISTS FOR ANTIOXIDANTS AND UV STABILIZERS

BACKGROUND OF THE INVENTION

Polymers have in the past and continue to provide an attractive substitute for the more traditional types of structural materials (e.g. wood or metals) because of relatively inexpensive materials and fabrication cost. As polymers continue to find new applications in, for example, the fabrication of automotive parts and building materials, they must also become more durable and capable of withstanding prolonged exposure to a variety of degradative forces. Degradation of polymers can be caused by exposure to light, heat, moisture and/or air. Such degradation is usually manifest by either a partial or total loss of structural integrity, changes in light transmission properties, changes in color, loss or reduction of flexibility and/or resiliency, or any combination of the above phenomena. Those attempting to avoid polymer degradation have generally selected from among three possible approaches: (a) elimination or reduction of the degradative forces; (b) isolation of the sensitive material from the degradative forces; or (c) modification of the polymer composition to enhance its resistance to the degradative forces. The latter approach is generally preferable since it does not require elaborate engineering nor structural changes in the polymer product environment.

As one might readily expect, the problems associated with the stabilization of different polymeric materials are affected to a greater extent by the functionality of the polymer and any unsaturation that may be present along the backbone or the side chains of such materials. For example, where the polymer contains unsaturation along its backbone and/or side chains, it is highly sensitive to oxidative degradation. Materials that are suitable to prevent oxidative degradation of dienic or unsaturated polymers do not necessarily have similar beneficial effects when incorporated within a polymeric material lacking such unsaturation. Similarly, stabilizers which are effective for polyolefins, such as polyethylene, may have little, if any, stabilizing effect upon dienic polymers or polymers having unsaturation along their backbone or side chain.

There are a variety of additives which have been disclosed in the past as suitable for enhancing polymer resistance to one or more degradative forces described hereinabove. These additives (hereinafter collectively referred to as "stabilizers") can usually by physically combined with or engrafted on the environmentally sensitive polymer thereby prolonging its useful life in its hostile degradative environment. It is not uncommon for polymers to contain a variety of stabilizer materials, (i.e. a stabilizer package), each being present for prevention on a particular degradative reaction. One of the more difficult to control of the degradative forces is the irradiation of polymers by ultraviolet light. The impact of such irradiation will, of course, vary depending upon the intensity and duration of exposure and thus, may manifest itself only after a prolonged interval. The irradiation of polymers with ultraviolet light can often times cause crosslinking of these materials, thereby reducing its resiliency and/or impact resistance. Changes in color and opacity are often affected by prolonged exposure of polymers to UV irradiation. While many materials are known and commercially available as stabilizers against ultraviolet light degradation, the degree of protection afforded by such agents is generally concentration dependent and may be geared to a particular limited class of material.

The prior art is replete with technical articles and patents directed to resolving this complex problem; see, for example, "Photodegradation, Photooxidation and Photostabilization of Polymers", B. Ranby and J. Raybeck, John Wiley & Sons, New York, NY (1975). Hindered amines and phenols are commonly used AO/UV stabilizers for rubber and polymeric materials. Various amides have also been found useful as antioxidants.

U.S. Pat. No. 3,665,031 discloses antioxidants such as amides of phenol substituted acids which are produced by reacting acid derivatives with amino compounds. U.S. Pat. No. 3,780,103 teaches the preparation of alkylhydroxybenzylamides. Amino-acid amides are also disclosed in U.S. Pat. Nos. 2,153,707 and 3,247,200. U.S. Pat. No. 4,310,429 discloses substituted α-amino-acetamides as stabilizers for organic materials, the disclosure of which is herein incorporated by reference. Further, U.S. Pat. No. 3,960,984, which is incorporated by reference, discloses amide oligomers as heat stabilizers for oxymethylene polymers.

The present invention relates to novel oligomeric amides and their method of preparation. The novel oligomeric amides are useful as stabilizers for polymers, particularly as synergists for other AO/UV stabilizers. Thus, it is the object of this invention to provide a novel stabilizer material suitable for enhancing the resistance of polymers to oxidation and photodegradation. It is a further object of this invention to provide oligomeric stabilizers which are relatively non-volatile and resistant to extraction by solvents. It is yet another object of this invention to provide a method for preparation of novel oligomeric amide stabilizers in a one-step synthesis and with good yield.

SUMMARY OF THE INVENTION

This invention relates to novel oligomeric amides and their method of preparation. The novel amide oligomers can be represented by the general formula:

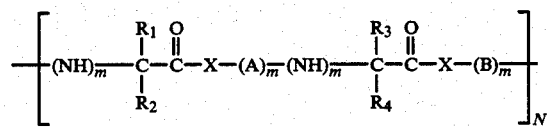

wherein $R_1$, $R_2$, $R_3$ and $R_4$ may be the same or different and represents alkyl, aralkyl, alkaryl or aryl radicals, and $R_1$ and $R_2$ or $R_3$ and $R_4$ together can be a cyclic alkyl group; A and B may be the same or different and represent alkylene radicals or

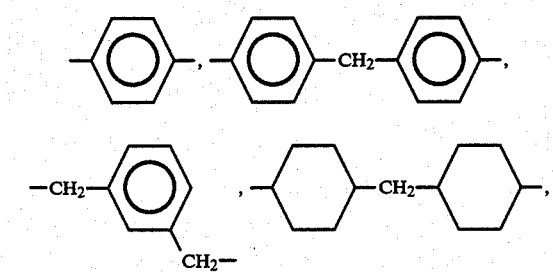

-continued

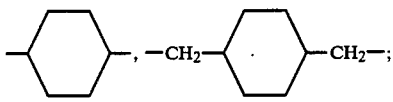

X represents —NH— or

m is 0 or 1; and n ranges from about 2 to about 100.

The amide oligomers can be prepared in a one-step synthesis by reacting a suitable amine with the appropriate ketone and a chlorinated hydrocarbon such as chloroform. These amides are useful as stabilizers for polymers, particularly as synergist for other AO/UV stabilizers.

DETAILED DESCRIPTION

The present invention relates to novel oligomeric amides which find utility as polymer stabilizers, either alone or as synergists for other antioxidants or ultraviolet stabilizers.

The novel oligomeric amides of this invention can be represented by the general formula:

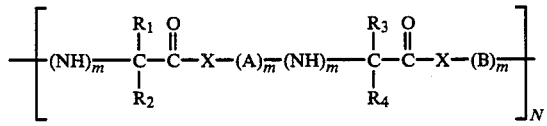

wherein $R_1$, $R_2$, $R_3$ and $R_4$ are the same or different and represent alkyl, aralkyl, alkaryl or aryl radicals containing 1–20 carbons, and further that $R_1$ and $R_2$ or $R_3$ and $R_4$ together can be a cyclic alkyl group; A and B are the same or different and represent alkylene radicals of 1–10 carbons or

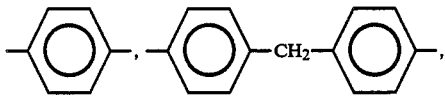

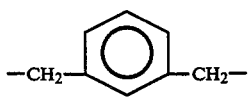

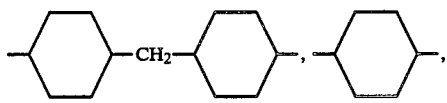

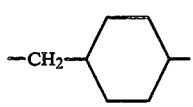

X represents —NH— or

m is 0 or 1; and n ranges from about 2 to about 100. The general formula above is meant to include all block polymers of the oligomeric amides, such as the AAA, ABA, AAB, ABB, and BAB types.

The oligomeric amides can be prepared by a novel one-step method of synthesis and in good yield. The synthesis is carried out, preferably in a closed vessel, by reacting suitable amines; such as, for example, bis(cyclohexylamines), bis(anilines), piperazines, and phenylenediamines; an appropriate ketone, such as, for example, acetone and 2-butanone; and a chlorinated hydrocarbon, such as, for example, chloroform. The synthesis is preferably carried out in methylene chloride or excess ketone and in the presence of a catalytic amount of benzyltriethylammonium chloride.

The oligomeric amides of this invention can be used to stabilize organic materials against oxidative degradation and photodegradation. Organic materials which may be stabilized include, for example, polymers and copolymers of butadiene, polyurethanes, polymers and copolymers of vinyl and vinylidene halides, polyamides, polystyrene, polyacrylonitrile, polymethacrylates, polycarbonates, phenylformaldehyde resins, polyepoxides, polyesters, polyolefins such as polyethylene and polypropylene, and the like. The oligomeric amides may be used alone or in combination with other stabilizers and additives, such as, antioxidants, color stabilizers, heat stabilizers, light stabilizers and the like. When employed in combination with many of these, a synergistic effect will be obtained. The oligomeric amides are particularly useful as synergist for hindered phenolic antioxidants such as, for example, 1,3,5-tris-(3',5'-di-t-butyl-4-hydroxybenzyl)isocyanurate.

The present oligomeric amides are compatible with conventional compounding ingredients such as processing oils, plasticizers, lubricants, fillers, reinforcing agents, curing agents, accelerators, antifoaming agents, rust inhibitors and the like. The oligomeric amides are readily incorporated into most organic materials and generally require no special processing. The oligomeric amides have a molecular weight of about 1000 or higher and are relatively non-volatile and resistant to extraction by solvents.

The amount of oligomer amide stabilizer employed will vary with the organic material to be stabilized and the particular amide used. In general, for effective stabilization of most organic materials, an amount of oligomeric amide ranging from about 0.01 percent to about 10 percent by weight based on the weight of the organic material will be employed. Preferably, the amount of oligomeric amide stabilizer used ranges between about 0.01 to about 2.5 percent by weight, and most preferably from about 0.1 to about 0.5 percent by weight.

The following Examples are presented to illustrate this invention it being understood that the Examples are to be interpreted in an illustrative and not a limitative sense.

EXAMPLE I

Preparation of poly[imino(1,1-dimethyl-2-oxo-1,2-ethanediyl)imino-1,4-cyclohexanediylmethylene-1,4-cyclohexanediyl].

In a 500 ml three-necked flask were charged 0.1 mole (21.0 g) of 4,4'-methylenebis(cyclohexylamine); 0.3 mole (17.4 g) of acetone; 0.1 mole (11.9 g) of chloroform; 100 ml of methylene chloride; and 1.6 grams of benzyltriethylammonium chloride (BTEAC). 40.0 grams of 50% aqueous sodium hydroxide solution were added while maintaining the temperature of the mixture below 0° C. The mixture was reacted overnight at 2°-3° C. and subsequently 100 ml of methylene chloride and 100 ml of water were added. The organic layer was separated using a separatory funnel. The aqueous layer was rinsed twice with 200 ml of methylene chloride. The organic layers were combined, washed twice with 200 ml of water, and dried over anhydrous magnesium sulfate to obtain 28.9 grams of white solid product.

The crude product was ground, washed with 200 ml of hexane, and filtered to obtain 20.8 grams of white solid having a softening point of 72° C. The product was found to have the following oligomeric structure by field desorption mass spectrum;

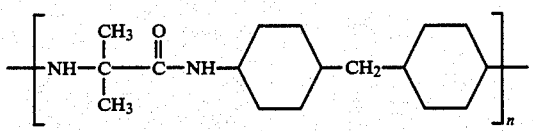

The product had number average molecular weight (Mn) of 1480 by vapor pressure osmometery.

EXAMPLE II

Preparation of poly[imino(1-ethyl-1-methyl-2-oxo-1,2-ethanediyl)imino-1,4-cyclohexanediylmethylene-1,4-cyclohexanediyl].

Following the procedure in Example I, 0.2 mole (42.0 g) of 4,4'-methylenebis(cyclohexyl amine) was reacted with 0.8 mole (57.7 g) of 2-butanone and 0.2 mole (23.8 g) of chloroform, in the presence of 100 ml of methylene chloride, 3.2 grams of BTEAC and 80 grams of 50% aqueous sodium hydroxide solution. After the usual work-up 27.4 grams of off-white solid were obtained. The product had a softening point of 65° C. and the following oligomeric structure (Mn 1070):

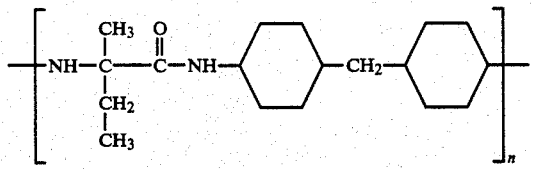

EXAMPLE III

Preparation of poly[imino(1,1-dimethyl-2-oxo-1,2-ethanediyl)imino-1,4-phenylenemethylene-1,4-phenylene].

Following the procedure in Example I, 0.1 mole (19.8 g) of 4,4'-methylenebis(aniline) was reacted with 0.4 mole (23.2 g) of acetone and 0.3 mole (35.7 g) of chloroform in the presence of 120 ml of methylene chloride, 3.0 grams of BTEAC, and 100 grams of 50% aqueous sodium hydroxide solution. After the usual work-up 22.2 grams of a brownish-yellow solid were obtained. The product had a softening point of 130° C. and the following oligomeric structure ($\overline{M}n$ 2050):

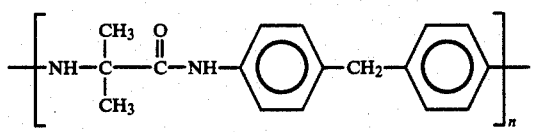

EXAMPLE IV

Preparation of poly[imino(1,1-dimethyl-2-oxo-1,2-ethanediyl)iminomethylene-1,3-phenylenemethylene].

Following the procedure in Example I, 0.1 mole (13.6 g) of m-xylylenediamine was reacted with 0.45 mole (25.4 g) of acetone and 0.1 mole (11.9 g) of chloroform in the presence of 50 ml of methylene chloride, 1.6 grams of BTEAC, and 40 grams of 50% aqueous sodium hydroxide solution. After the usual work-up 19.4 grams of off-white solid were obtained. The product had a softening point of 50° C. and the following oligomeric structure ($\overline{M}n$ 1500):

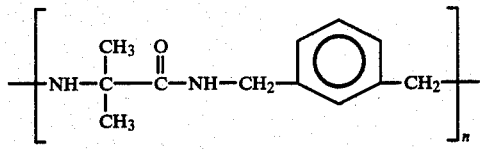

EXAMPLE V

Preparation of poly[imino(1,1-dimethyl-2-oxo-1,2-ethanediyl)imino-1,4-cyclohexanediylmethylene-1,4-cyclohexanediylimino(1,1-dimethyl-2-oxo-1,2-ethanediyl)iminomethylene-1,3-phenylenemethylene].

Following the procedure in Example I, 0.05 mole (6.8 g) of m-xylylenediamine and 0.05 mole (10.5 g) of 4,4'-methylenebis(cyclohexylamine) were reacted with 0.5 mole (29.0 g) of acetone and 0.1 mole (11.9 g) of chloroform in the presence of 100 ml of methylene chloride, 1.6 grams of BTEAC, and 40 grams of 50% aqueous sodium hydroxide solution. After the usual work-up 16.6 grams of off-white solid were obtained. The product had a softening point of 75° C. and the following oligomeric structure:

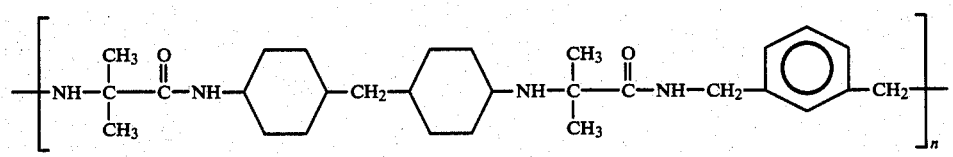

EXAMPLE VI

Preparation of poly[1,4-piperazinediyl(1-oxo-2,2-dimethyl-1,2-ethanediyl)].

Following the procedure in Example I, 0.2 mole (17.2 g) of piperazine was reacted with 0.6 mole (34.8 g) of acetone and 0.2 mole (23.9 g) of chloroform in the presence of 100 ml of methylene chloride, 3.2 grams of BTEAC, and 80 grams of 50% aqueous sodium hydroxide solution. After the usual work-up 8.1 grams of off-white solid were obtained. The product had a softening point of 164° C. and the following oligomeric structure ($\overline{M}n$ 1030):

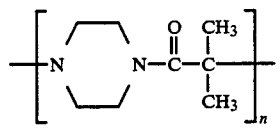

EXAMPLE VII

Preparation of poly[imino(1,1-dimethyl-2-oxo-1,2-ethanediyl)imino-1,4-phenylene].

Following the procedure in Example I, 0.1 mole (10.8 g) of p-phenylenediamine was reacted with 17.4 grams of acetone and 11.9 grams of chloroform in the presence of 100 ml of methylene chloride, 1.6 grams of BTEAC, and 40 grams of 50% aqueous sodium hydroxide solution. After the usual work-up, 15.3 grams of brown solid were obtained. The product had a softening point of 180° C. and the following oligomeric structure ($\overline{M}n$ 1030):

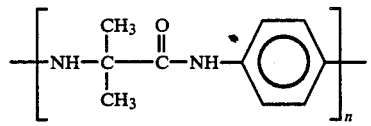

The product obtained in Example V was evaluated for its stabilizing properties in polypropylene by oven-aging at 125° C. and the xenon weatherometer. Test samples were prepared by mixing the stabilizer with 100 parts by weight polypropylene following the recipes given in Table I. The samples were pressed in 20 mil thick sheets and cut into plaques for evaluation. In the oven-aging test, time to catastrophic crumbling of the plaques was measured and reported as days to failure. In the xenon weatherometer test the number of hours resulting in a loss of 50% of the original tensile strength is reported.

TABLE I

| Stabilizer | Amount (Parts by Weight) | Oven-Aging 125° C. (days) | Xenon Weatherometer (hours) |
|---|---|---|---|
| none | — | 2 | 100 |
| Goodrite ® 3114 [1,3,5-tris(3',5'-di-t-butyl-4-hydroxybenzyl)isocyanurate] | 0.1 | 34 | 440 |
| Goodrite ® 3114 | 0.25 | 67 | 600 |
| Example V | 0.1 | 2 | 220 |
| Example V | 0.25 | 2 | 400 |
| Example V | 0.125 } | 69 | 880 |
| Goodrite ® 3114 | 0.125 | | |

We claim:

1. Oligomeric amides having the general formula

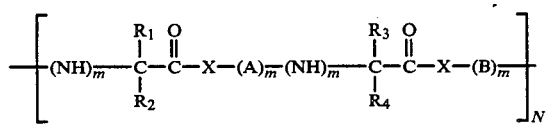

wherein $R_1$, $R_2$, $R_3$ and $R_4$ are the same or different and are selected from the group consisting of alkyl, aralkyl, alkaryl or aryl radicals containing 1-20 carbons, and $R_1$ and $R_2$ or $R_3$ and $R_4$ together can be a cyclic alkyl group; A and B are the same or different and are selected from the group consisting of alkylene radicals containing 1-10 carbons,

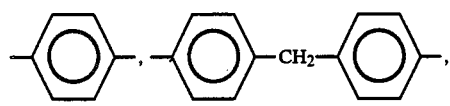

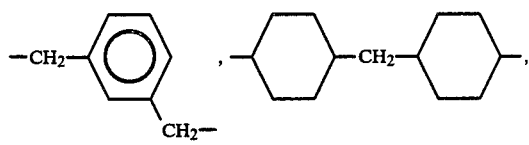

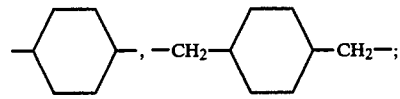

X is selected from the group consisting of —NH— and

m is 0 or 1; and n ranges from about 2 to about 100.

2. Oligomeric amides of claim 1 wherein X is

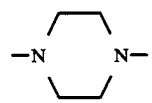

and m is 0.

3. Oligomeric amides of claim 1 represented by the general formula

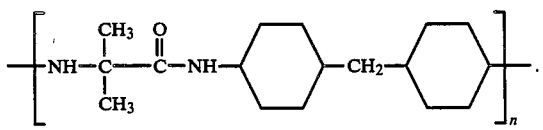

4. Oligomeric amides of claim 1 represented by the general formula

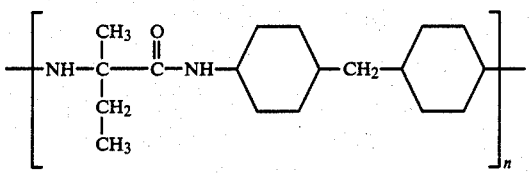

5. Oligomeric amides of claim 1 represented by the general formula

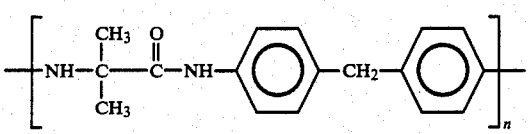

6. Oligomeric amides of claim 1 represented by the general formula

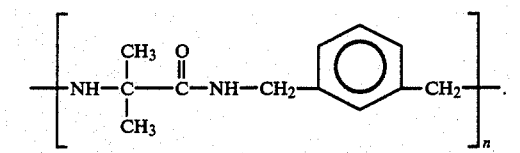

7. Oligomeric amides of claim 1 represented by the general formula

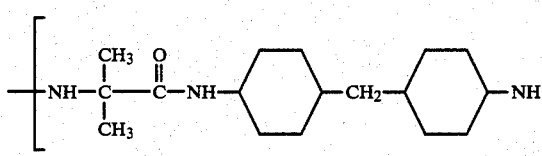

8. Oligomeric amides of claim 1 represented by the general formula

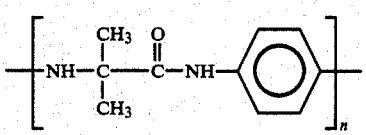

9. A composition of matter essentially containing an organic material subject to oxidative degradation and photodegradation and an effective amount of an oligomeric amide stabilizer having the general formula

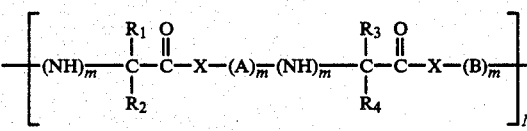

wherein $R_1$, $R_2$, $R_3$ and $R_4$ are the same or different and are selected from the group consisting of alkyl, aralkyl, alkaryl or aryl radicals containing 1–20 carbons, and $R_1$ and $R_2$ or $R_3$ and $R_4$ together can be a cyclic alkyl group; A and B are the same of different and are selected from the group consisting of alkylene radicals containing 1–10 carbons,

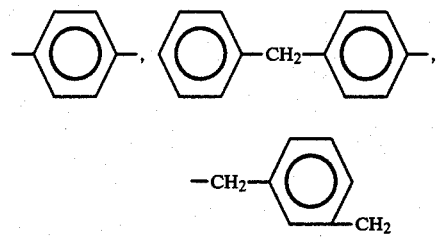

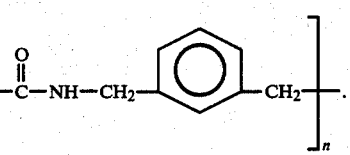

X is selected from the group consisting of —NH— and $$-N\underset{\phantom{XXX}}{\diagup\kern-1em\diagdown} N-;$$

m is 0 or 1; and n ranges from about 2 to about 100; said organic material is selected from the group consisting essentially of polymers and copolymers of butadiene, polyurethanes, polymers and copolymers of vinyl and vinylidene halides, polyamides, polystyrene, polyacrylonitrile, polymethacrylates, polycarbonates, phenylformaldehyde resins, polyepoxides, polyesters, polyolefins, and mixtures thereof.

10. A composition of claim 9 wherein the material is selected from the group consisting essentially of polymers and copolymers of butadiene, polyethylene, and polypropylene.

11. A process for the preparation of oligomeric amides having the general formula

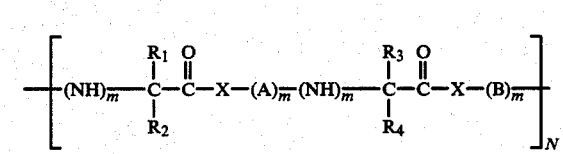

wherein $R_1$, $R_2$, $R_3$ and $R_4$ are the same or different and are selected from the group consisting of alkyl, aralkyl, alkaryl or aryl radicals containing 1–20 carbons, and $R_1$ and $R_2$ or $R_3$ and $R_4$ together can be a cyclic alkyl group; A and B are the same or different and are selected from the group consisting of alkylene radicals containing 1–10 carbons,

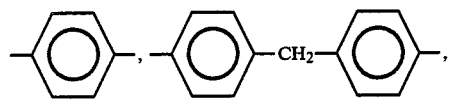

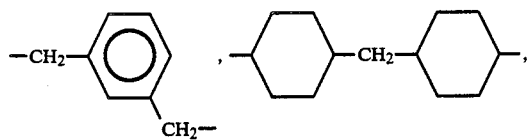

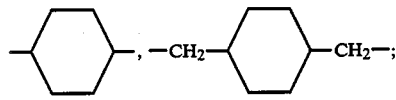

X is selected from the group consisting of —NH— and

m is 0 or 1; and n ranges from about 2 to about 100, which comprises reacting in one step an amine, a ketone, and chloroform.

12. A process of claim 11 wherein the amine is selected from the group consisting of bis(cyclohexylamines), bis(anilines), piperazines, and phenylenediamines.

13. A process of claim 11 wherein the ketone is selected from the group consisting of acetone and 2-butanone.

14. Oligomeric amides of claim 1 represented by the general formula

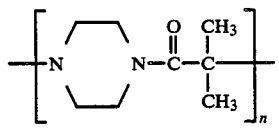

* * * * *